United States Patent [19]

Agback et al.

[11] Patent Number: 4,559,330

[45] Date of Patent: Dec. 17, 1985

[54] USE OF 3,3′-AZO-BIS-(6-HYDROXY BENZOIC ACID) AS A DRUG AND PHARMACEUTICAL COMPOSITIONS CONTAINING THE SAME

[75] Inventors: Karl H. Agback; Tore Natvig, both of Uppsala, Sweden; Sidney C. Truelove, Kirtlington, England

[73] Assignee: Pharmacia AB, Uppsala, Sweden

[21] Appl. No.: 247,252

[22] Filed: Mar. 25, 1981

[30] Foreign Application Priority Data

Mar. 26, 1980 [SE] Sweden .............................. 8002322

[51] Int. Cl.$^4$ .......................................... A61K 31/655
[52] U.S. Cl. .................................................... 514/166
[58] Field of Search ......................................... 424/226

[56] References Cited

U.S. PATENT DOCUMENTS 4,312,806  1/1982  Lambert et al. .................... 424/154

Primary Examiner—Frederick E. Waddell
Attorney, Agent, or Firm—Stiefel, Gross, Kurland & Pavane

[57] ABSTRACT

A method of treating inflammatory diseases such as ulcerous colitis, comprising administration of 3,3′-azo-bis-(6-hydroxy benzoic acid) of the formula:

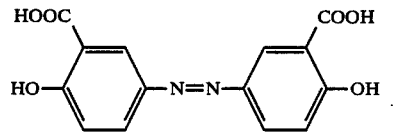

or pharmaceutically acceptable salts thereof. Pharmaceutical compositions, especially for oral administration, contain said compound, or pharmaceutically acceptable salts thereof, together with pharmaceutically acceptable carriers and/or adjuvants.

13 Claims, No Drawings

USE OF 3,3'-AZO-BIS-(6-HYDROXY BENZOIC ACID) AS A DRUG AND PHARMACEUTICAL COMPOSITIONS CONTAINING THE SAME

The present invention relates to a method for treating inflammatory intestinal diseases, such as ulcerous colitis, by administration of 3,3'-azo-bis-(6-hydroxy benzoic acid), or pharmaceutically acceptable salts thereof, and to pharmaceutical compositions containing said compound or pharmaceutically acceptable salts thereof.

The disease ulcerous colitis is a serious chronic intestinal disease, which has a fluctuating course of development and is localized to the large intestine. The method of treatment of ulcerous colitis and similar inflammatory intestinal diseases, which is recommended at the present state of the art, is oral administration of salicylazosulfapyridine (sulphasalazine). The main effect of this treatment is a prolongation of the periods when the patient is free of symptoms. The characteristic property of salicylazosulfapyridine is that it passes the stomach and the small intestine essentially intact to finally exert a local effect in the large intestine. It has been found that the microorganisms present in the large intestine efficiently reduce and split off the azo bond of the salicylazosulfapyridine while forming sulfapyridine and 5-amino-salicylic acid. These substances are then absorbed in the blood, and they also to a certain extent are subjected to further metabolisation. A disadvantage of this method of treatment is that salicylazosulfapyridine in certain cases can give troublesome side effects, which usually are assigned to absorbed sulfapyridine.

It is an object of the present invention to reduce or eliminate the side effects of salicylazosulfapyridine while maintaining or increasing the antiinflammatory effect of this substance. The invention is based on the finding that rectal administration of equivalent amounts of 5-amino-salicylic acid and salicylazosulfapyridine respectably give the same clinical effect on inflammatory intestinal diseases such as ulcerous colitis. This indicates that the active component of salicylazosulfapyridine can be 5-amino-salicylic acid. However, it is not possible to use 5-amino-salicylic acid as an oral drug, since the compound in question is absorbed quantitatively in the small intestine and thus never can reach the inflamed area in the large intestine. The same is true for most simple derivatives of 5-amino-salicylic acid.

It has now according to the invention surprisingly been found that a special derivative of 5-amino-salicylic acid, namely 3,3'-azo-bis(6-hydroxy benzoic acid) of formula I

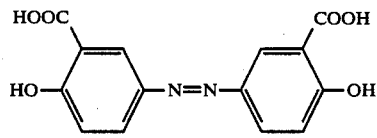

has the desired property, i.e. it can be transported to the large intestine uneffected and be reduced to 5-amino-salicylic acid therein.

The compound of formula I is a substance which is known per se, and which has found commercial use as a dyestuff. However, it has found no use for medical purposes, and this has not either been possible since the known methods of preparation do not allow preparation of an end product of sufficient purity for such use.

The present invention thus relates to the compound 3,3'-azobis-(6-hydroxy benzoic acid) and its pharmaceutically acceptable salts for use in the treatment of inflammatory intestinal diseases, especially in the large intestine. The invention also relates to pharmaceutical compositions, especially for oral administration, which contain 3,3'-azo-bis(6-hydroxy benzoic acid) or a pharmaceutical acceptable salt thereof, possibly in combination with an organic or inorganic inert carrier material suitable for oral administration and/or possible additional conventional adjuvants. The pharmaceutical compositions can, for example, have the form of tablets, dragées, capsules, etc. The pharmaceutical compositions can be prepared in a manner well known to any person skilled in the art by mixing the compound of formula I and/or a pharmaceutical acceptable salt thereof, for example the sodium or potassium salt, with the desired carrier material and/or adjuvants and transforming the mixture thus obtained to a suitable galenic form. The dosage is adjusted to the needs and desires in the individual situation, but doses of 0.5–10 g, preferably 1–5 g per day for adult patients can be mentioned as a general indication. The daily dose is preferably administrated in the form of several (for example 3 to 4) part doses. It is usually sufficient with a lower dosage than in conventional salicylazosulfapyridine treatment.

For use according to the present invention the compound of formula I and its pharmaceutically acceptable salts are preferably prepared by means of the method of synthesis disclosed in our simultaneously herewith filed patent application Ser. No. 247,402, since this method of synthesis makes it possible to prepare the compound of formula I in sufficiently pure form in simple manner. This method of synthesis is also illustrated in Example 1 below.

The invention will be illustrated by means of the following non-limiting examples.

EXAMPLE 1

The di-sodium salt of 3,3'-azo-bis-(6-hydroxy benzoic acid) of pharmaceutically acceptable purity was prepared as follows:

98.5 g of methyl-2-hydroxy-5-nitro-benzoate were dissolved in 250 ml of pyridine, whereupon 68.5 g of methane sulfonylchloride were added. After heating to 50° C. for 10 minutes the solution was poured on 5N ice-cooled hydrochloric acid. The oil formed was extracted with chloroform. The chloroform phase was washed with water, dried and evaporated. 50 ml of toluene were added and evaporated. This was repeated once and the oil crystallized.

132 g of the nitro compound were hydrogenated in 500 ml of acetic acid and 3 g of 10% palladium-on-carbon at 1–3 at. After the theoretical amount of hydrogen gas had been consumed the mixture was filtered and evaporated. It was dissolved in 1 liter of isopropanol at 65° C., whereupon HCl in ethanol was added. The hydrochloride crystallized upon cooling. After filtering the substance was shaken with sodium carbonate in water and chloroform. The chloroform phase was evaporated. The amine was recrystallized from methanol/water. Yield: 93 g of methyl-3-amino-6-methane sulfonyloxy-benzoate.

12.2 g of methyl-3-amino-6-methane sulfonyloxy-benzoate (prepared according to Example 1), 75 ml of 2N hydrochloric acid and 200 g of ice were diazotized at 0° C. with 3.5 g sodium nitrite in 20 ml of water. The diazonium salt solution was rapidly mixed with a freshly prepared solution of 15.2 g of methyl salicylate, 12 g of 85% potassium hydroxide and 1 liter of ice-water while stirring vigorously. The coupling solution was acidified with hydrochloric acid after about 15 seconds. The precipitated oily product was extracted with chloroform. After drying, evaporation and re-crystallization from 2-butanone the title substance was obtained in a yield of 12.8 g.

624 g of this substance were added in portions during 15 minutes while boiling to 3 liter of water and 428 g of sodium hydroxide. After boiling for 30 minutes 367 ml of acetic acid were added during 15 minutes to pH 6. The suspension was stirred for 1.5 h without cooling, the temperature falling to 70° C. After cooling to 30° C. the suspension was filtered and washed with 700 ml of methanol. After drying di-sodium-3,3'-azo-bis(6-hydroxy benzoate) was obtained in a yield of 520 g and with a purity of >99%.

EXAMPLE 2

The following components are mixed in the proportions indicated, whereupon tablets containing 250 mg of active substance are pressed in conventional manner.

| | |
|---|---|
| 3,3'-azo-bis-(6-hydroxy benzoic acid) (di-sodiumsalt) | 62% |
| corn starch | 17% |
| milk sugar | 17% |
| polyvinylpyrrolidone | 3% |
| magnesium stearate | 1% |

EXAMPLE 3

Di-sodium-3,3'-azo-bis(6-hydroxy benzoate) was in conventional manner filled in gelatine capsules with 125 mg per capsule.

EXAMPLE 4

The ability of 3,3'-azo-bis(6-hydroxy benzoic acid) to pass the stomach and the small intestine intact, as well as to release 5-amino-salicylic acid was investigated in the following way:

6 dogs, weighting between 10.5 and 14.0 kg, were orally administrated with 100 mg/kg body weight of 3,3'-azo-bis(6-hydroxy benzoic acid) in gelatine capsules. Urine was collected within the time intervals 0–7 h, 7–22 h and 22–48 h. Blood samples were taken after 7, 22 and 48 h respectively. The total excreted amount of intact 3,3'-azo-bis(6-hydroxy benzoic acid) was on the average only 0.58% of the dose given. Thereof 0.33% was obtained during 0–7 h, 0.24% during 7–22 h, and 0.01% during 22–48 h. The blood concentration was less than 1 μg/ml. This points to a very insignificant absorption of the agent from the stomach and the small intestine. The excreted amount of 5-amino-salicylic acid, including the secondary metabolite 5-acetamido salicylic acid, was during 0–7 h 0.85%, during 7–22 h 10.0% and during 22–48 h 7.2%, in total 18% of the theoretically calculated amount.

Since it is known that only about 20% of the total amount of 5-amino-salicylic acid is absorbed from the large intestine, the results indicate that 3,3'-azo-bis(6-hydroxy benzoic acid) practically quantitatively is split into 5-amino-salicylic acid.

EXAMPLE 5

The results of the animal test of Example 4 were confirmed by the following corresponding test on humans.

8 healthy male volunteers were orally administered with 500 mg each of 3,3'-azo-bis-(6-hydroxy benzoic acid) in gelatine capsules. Serum samples were taken and urine collected over 3 days. The mean total amount excreted of intact 3,3'-azo-bis-(6-hydroxy benzoic acid) was 1.3% of the dose given. The mean total amount of 5-acetamido salicylic acid and 5-amino salicylic acid was 27%. The maximum serum level of 3,3'-azo-bis-(6-hydroxy benzoic acid) was observed after 1 h and was 2.0 μg/ml (mean level).

What we claim is:

1. A method of treating inflammatory intestinal diseases, comprising administering to a patient in a need thereof therapeutically effective amount of 3,3'-azo-bis-(6-hydroxy benzoic acid) or a pharmaceutically acceptable salt thereof.

2. The method of claim 1 comprising oral administration of said substance.

3. A method of treating ulcerous colitis, comprising administering to a patient in a need thereof a therapeutically effective amount of 3,3'-azo-bis-(6-hydroxy benzoic acid), or a pharmaceutically acceptable salt thereof.

4. The method of claim 3 comprising oral administration of said substance.

5. A pharmaceutical composition comprising 3,3'-azo-bis-(6-hydroxy benzoic acid) or pharmaceutically acceptable salts thereof, in combination with at least one pharmaceutically acceptable carrier or adjuvant.

6. A composition for treating inflammatory intestinal diseases, comprising 3,3'-azo-bis-(6-hydroxy benzoic acid) or pharmaceutically acceptable salts thereof, in combination with at least one pharmaceutically acceptable carrier or adjuvant.

7. A composition for treating ulcerous colitis, comprising 3,3'-azo-bis-(6-hydroxy benzoic acid) or pharmaceutically acceptable salts thereof in combination with at least one pharmaceutically acceptable carrier or adjuvant.

8. An oral composition for treating inflammatory diseases in the large intestine, comprising 3,3'-azo-bis-(6-hydroxy benzoic acid) or pharmaceutically acceptable salts thereof, in combination with at least one pharmaceutically acceptable carrier or adjuvant.

9. A method according to claims 1 or 3 wherein said therapeutically effective amount is 0.5–10 g per day for adult patients.

10. A method according to claim 3 or claim 4 wherein said therapeutically effective amount is 0.5–10 g per day for adult patients.

11. A method according to claim 9 wherein said inflammatory intestinal diseases are in the large intestine.

12. A method according to any one of claims 1–4 wherein said salt is the disodium salt.

13. A composition according to any one of claims 5–8 and 9 wherein said salt is the disodium salt.

* * * * *

UNITED STATES PATENT AND TRADEMARK OFFICE

CERTIFICATE EXTENDING PATENT TERM
UNDER 35 U.S.C. 156

Patent No.    : 4,559,330

Dated         : December 17, 1985

Inventor(s)   : Karl H. Agback et al

Patent Owner  : Pharmacia AB

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

592 DAYS with all rights pertaining thereto as provided by 35 U.S.C. 156 (b).

I have caused the seal of the Patent and Trademark Office to be affixed this 30th day of December 1991.

Harry F. Manbeck, Jr.
Assistant Secretary and Commissioner
  of Patents and Trademarks